United States Patent [19]

Donald

[11] 3,959,277
[45] May 25, 1976

[54] DIIMIDAZOPYRAZINES AND TETRACARBOXAMIDOPYRAZINES

[75] Inventor: Dennis Scott Donald, Mendenhall, Pa.

[73] Assignee: E. I. Du Pont de Nemours and Company, Wilmington, Del.

[22] Filed: Feb. 20, 1974

[21] Appl. No.: 444,542

Related U.S. Application Data

[63] Continuation-in-part of Ser. No. 271,938, July 14, 1972, Pat. No. 3,808,209.

[52] U.S. Cl. .................... 260/250 BC; 252/301.25; 260/250 B; 260/250 R; 260/250 BN
[51] Int. Cl.² ............. C07D 241/26; C07D 241/250
[58] Field of Search ... 260/250 BC, 250 R, 250 BN; 252/301.2 W

[56] References Cited
UNITED STATES PATENTS

| | | | |
|---|---|---|---|
| 3,017,412 | 1/1962 | Daglish | 260/250 BN |
| 3,369,018 | 2/1968 | Giovanoel | 260/250 BN |
| 3,657,231 | 4/1972 | Booth | 260/250 BN |
| 3,660,397 | 5/1972 | Jones et al. | 260/250 BN |

*Primary Examiner*—Raymond V. Rush
*Assistant Examiner*—D. B. Springer

[57] ABSTRACT

Diimidazopyrazines of the formula:

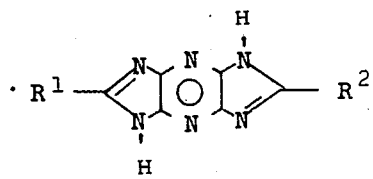

wherein $R^1$ and $R^2$ are selected from the group consisting of lower alkyl and aryl of 6 to 12 carbons which may be optionally substituted are described. These compounds are useful as brightening agents. They are prepared from tetracarboxamidopyrazines of the formula:

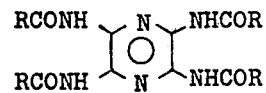

wherein the R's are as specified above for $R^1$ and $R^2$.

10 Claims, No Drawings

DIIMIDAZOPYRAZINES AND TETRACARBOXAMIDOPYRAZINES

CROSS-REFERENCE TO RELATED APPLICATION

This is a continuation-in-part of my copending application Ser. No. 271,938, filed July 14, 1972, now U.S. Pat. No. 3,808,209 issued Apr. 29, 1974.

BACKGROUND OF THE INVENTION

1. Field of the Invention

This invention relates to compounds containing the diimidazo [4,5-b:4',5'-e]pyrazine nucleus, a novel, tricyclic, heterocyclic ring system, and to their tetracarboxamidopyrazine precursors.

2. Description of the Prior Art

Compounds of the diimidazo [4,5-b:4',5'-e]pyrazine type have not been disclosed in the prior art. The closest disclosures are:

1. Schipper and Day, Elderfield's "Heterocyclic Compounds", Vol. 5, p. 274 (Wiley, 1957). Diacyl derivatives of o-phenylenediamine are converted to benzimidazole by heating in an atmosphere of nitrogen in accordance with the following equation:

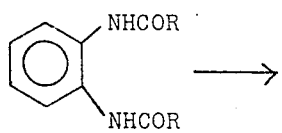

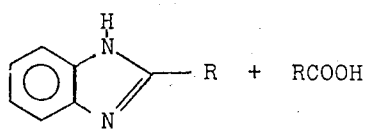

2. Schipper and Day, *J. Am. Chem. Soc.*, Vol. 74, p. 350 (1952). Reaction of 2,3-diamino-5,6-dimethylpyrazine with excess carboxylic acid halides in boiling xylene gave 2-substituted 1H-imidazo-[4,5-b]pyrazines:

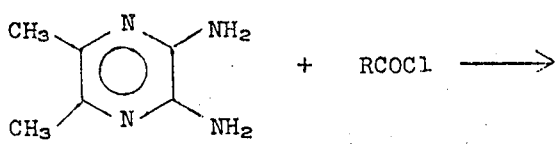

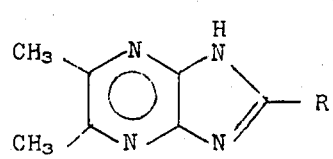

where R = alkyl or phenyl.

SUMMARY OF THE INVENTION

The products of the invention are diimidazopyrazines of the formula

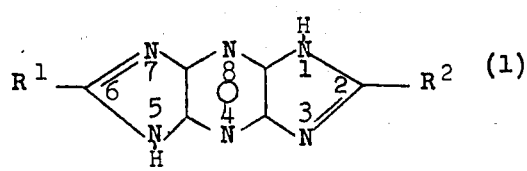

wherein $R^1$ and $R^2$ are each selected from the group consisting of lower alkyl and aryl of 6 to 12 carbons, optionally substituted with lower alkyl, lower alkoxy, phenoxy, fluoro, chloro, bromo, or nitro.

The invention also includes tetracarboxamidopyrazines of the formula

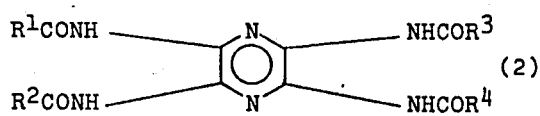

wherein $R^1$, $R^2$, $R^3$ and $R^4$ are the same as $R^1$ and $R^2$ above. "Lower alkyl" and "lower alkoxy" are defined, respectively, as alkyl of up to eight carbons and alkoxy of up to eight carbons.

DETAILED DESCRIPTION OF THE INVENTION

As will be obvious to those skilled in the art, compounds of formula (1) can also exist in the interconvertible tautomeric forms represented by formulas (3), (4) and (5):

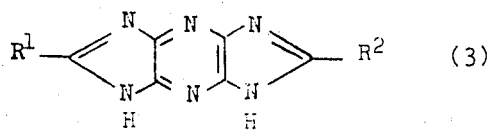

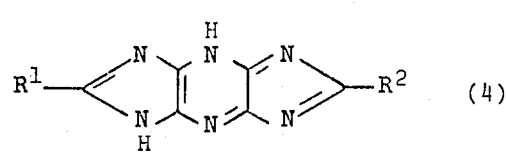

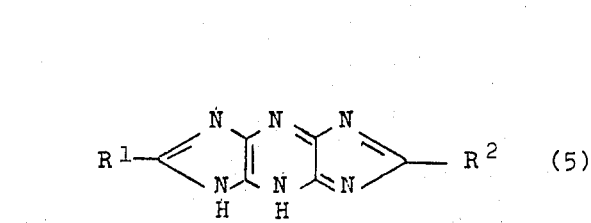

The invention includes all these tautomeric forms. Since the tautomer of formula (1) is believed to predominate, this formula is used throughout the specification and claims to designate the product in any tautomeric form.

The tetracarboxamidopyrazines of this invention are prepared by reacting tetraaminopyrazine with a carboxylic acid chloride of the formula RCOCl, in accordance with the equation:

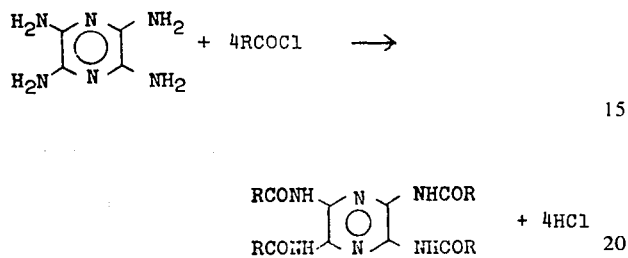

Best results are obtained with between four and five moles of cid chloride per mole of tetraaminopyrazine, i.e., 100–125% of the stoichiometric amount. When more than about a 25% excess of acid chloride is used, products containing more than one acyl group per amino group tend to be formed.

The process is conveniently carried out by adding the acid chloride in portions to a stirred slurry of tetraaminopyrazine in enough pyridine to maintain a fluid system at about 0°–10°C. The mixture can then be allowed to warm gradually to ambient temperature, at which point the reaction is usually essentially complete. If desired, the mixture can be stirred at ambient temperature, or at higher temperatures up to about 75°C., to insure completion of the reaction. The tetracarboxamide can be isolated by drowning the mixture in water, filtering, washing the solid on the filter, and recrystallizing if desired.

Examples of suitable R groups in the carboxylic acid chloride and the resulting tetracarboxamidopyrazines include lower alkyls such as methyl, ethyl, isopropyl, t-butyl, 1-ethylpentyl, and octyl; aryls such as phenyl, 1- and 2-naphthyl, and 2-, 3-, and 4-biphenylyl; and substituted aryls such as o-, m-, and p-tolyl, 3,5-di-t-butylphenyl, 4-ethyl-1-naphthyl, 3-isopropyl-2-biphenylyl, 2,4-dimethoxyphenyl, 3-butoxy-2-naphthyl, 4'-(2-methylhexyloxy)-4-biphenylyl, 4-methoxy-3'-biphenylyl, 6-t-butyl-3-methoxyphenyl, o-, m-, and p-phenoxyphenyl, o-, m-, p-chlorophenyl, 3,5-dichlorophenyl, 4-chloro-1-naphthyl, pentachlorophenyl, 2',3'-dichloro-4-biphenylyl, 2-chloro-3-fluorophenyl, 2',3', 4', 5',6'-pentachloro-3-biphenylyl, o-, m-, and p-fluorophenyl, 2,6-difluorophenyl, 1-fluoro-2-naphthyl, 2,4,5-trifluorophenyl, 2,3,5,6-tetrachlorophenyl, o-, m-, and p-bromophenyl, 3-, 4-, 5-, 6-, and 8-bromo-1-napthyl, 3,5-dibromophenyl, 5-bromo-2-chlorophenyl, 3-bromo-4-fluorophenyl, 4-bromo-3-fluoro-2-naphthyl, 2'-bromo-2-biphenylyl, 3-bromo-4-ethoxyphenyl, 5-chloro-2-ethylphenyl, o-, m-, and p-nitrophenyl, 2-, 3-, 4-, 5-, 6-, 7-, and 8-nitro-1-naphthyl, 2-fluoro-4-nitrophenyl, 4,5-dinitro-1-naphthyl, 6-methyl-5-nitro-1-naphthyl, 4'-methyl-2'-nitro-4-biphenylyl, 3-butoxy-4-nitrophenyl, 5-bromo-2-nitrophenyl, and 2'-chloro-4'-nitro-2-biphenylyl.

The alkyl and alkoxy groups preferably contain from one to four carbon atoms. Phenyl is the preferred aryl group. Aryl groups that are substituted will preferably contain at most two substitutents, except when the substituent is fluoro or chloro, in which case up to five substituents are equally preferred. Chloro is the preferred halo substituent, because of the effect that it has on the fluorescent properties of the products.

The 2,6-disubstituted 1H,5H-diimidazo[4,5-b:4',5'-e]pyrazines of this invention are prepared by heating the corresponding tetracarboxamidopyrazines of formula (2) to a temperature at which the corresponding carboxylic acid, RCOOH, is formed and eliminated according to the following equation:

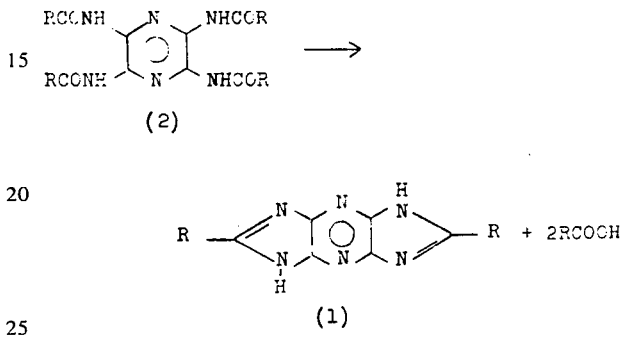

In this process two moles of the carboxylic acid, RCOOH, are formed per mole of reactant and per mole of product.

Each compound of formula (2) has a decomposition temperature, that is, a characteristic temperature or narrow temperature range at which it eliminates two moles of the carboxylic acid RCOOH and cyclizes to form a diimidazopyrazine of formula (1). For the purpose of further discussion, this temperature will be designated $T_p$. This temperature can be determined on a small sample in a sealed melting-point tube, by thermogravimetric analysis (TGA), or by differential thermal analysis (DTA). DTA shows that the process is endothermic.

In the absence of an added diluent, conversion of the tetracarboxamide of formula (2) to the diimidazopyrazine of formula (1) is best carried out at $T_p$ or slightly higher. Temperatures down to about 10°C. below $T_p$ can be used, but several hours may be required for completion. With small amounts of reactant there is usually no point in going much above $T_p$, since the reaction proceeds rapidly at $T_p$. With larger amounts of reactant, to transfer heat at a reasonable rate to all parts of the material, external temperatures about 25°C., or even about 50°C., above $T_p$ can be used, provided undesirable side reactions are not promoted thereby. The practical, operable temperature range is therefore between about 10°C. below $T_p$ and 50°C. above $T_p$. The process is usually conducted at atmospheric pressure, although subatmospheric or superatmospheric pressures can be used, if desired.

The process can be carried out in any of a number of types of apparatus for heating a solid or liquid reaction mixture and separating by condensation the relatively volatile carboxylic acid by-product. The process can be conducted with the undiluted tetracarboxamide or in the presence of a liquid diluent. It is convenient to use a diluent with relatively large quantities of the reactant in order to realize better heat transfer and better control of the reaction. If a diluent is used, it is preferably not a solvent for the starting material. Phenyl sulfone and commercially available heat-transfer liquids such as biphenyl/phenyl ether mixtures are suitable diluents.

When a diluent, such as phenyl sulfone, is used, it is sometimes possible to carry out the process at temperatures as much as 50°C. below $T_p$. This fact confers a special advantage when the starting tetracarboxamidopyrazine tends to undergo side reactions in the neighborhood of $T_p$. The operable temperature range in the presence of such a diluent is therefore between about 50°C. below $T_p$ and 50°C. above $T_p$. For tetracarboxamidopyrazines that undergo side reactions at or above $T_p$, the preferred temperatures will be in the lower part of this range.

The progress of the reaction can be followed by watching the volatilization and condensation of the byproduct carboxylic acid. After vacuum drying (or filtration, washing, and drying, if a diluent is used), the diimidazopyrazine is sometimes obtained in a form that is pure enough for many purposes. It can be recrystallized if desired from hot dilute aqueous sodium hydroxide. The initial product obtained in such a recrystallization is a sodium salt, in which hydrogen on nitrogen has been replaced by sodium. On neutralization with acid, and for some compounds simply on treatment with water, the sodium salt reverts to the dihydrogen compound of the invention. Also, and advantageously, the product can be recrystallized from dilute aqueous potassium hydroxide.

The diimidazopyrazine products of this invention are fluorescent in the solid state and in solution and are useful as brightening agents. Suitable substrates for these brightening agents include fabrics of a wide variety and paper.

EXAMPLES OF THE INVENTION

The following examples, illustrating the preparation and use of the novel products of this invention, are given without any intention that the invention be limited thereto. All parts and percentages are by weight unless otherwise specified.

EXAMPLE 1

A. Preparation of tetrabenzamidopyrazine:

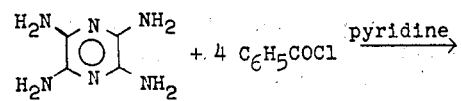

A slurry of 1.40 g of tetraaminopyrazine in 25 ml. of pyridine was cooled in an ice bath, and 6.0 ml of benzoyl chloride was added dropwise with stirring at such a rate that the temperature did not rise above 5°C. The ice bath was removed, and stirring was continued. The temperature rose over a period of 30 minutes to 20°C., at which point it rose to 60°C. within a few minutes. The mixture was cooled in ice, and the temperature dropped to 20°C. Stirring was continued for 30 minutes, after which the ice bath was again removed. The temperature rose slowly to ambient temperature and remained constant for 1 hour. The yellow slurry was poured into 150 ml. of water, and the mixture was filtered. The material on the filter was washed thoroughly with water and air-dried overnight, to give 5.50 g. (99%) the pale-yellow tetrabenzamidopyrazine as a powdery solid.

Anal. Calcd. for $C_{32}H_{24}O_4N_6$: C, 69.05; H, 4.35; N, 15.10. Found: C, 69.08; H, 4.24; N, 14.79; C, 69.29; H, 4.24; N, 14.77.

Recrystallization of part of the material from dimethylformamide gave the product in the form of white microcrystals. The recrystallized sample was analyzed further to give:

IR (KBr): $3.06\mu$ (—NH); $3.24\mu$ (—CH); $4.97\mu$, $6.58\mu$

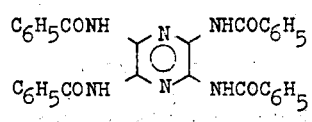

$6.19\mu$, $6.29\mu$, $6.71\mu$ (aromatic —C=C— and/or —C=N).

UV ($\lambda$ max/DMF): $337m\mu$ ($\epsilon = 20,300$).

NMR (DMSO-d$_6$): multiplet centered at $7.13\delta$ (5H); singlet, $10.3\delta$ (1H).

HRMS: molecular ion, $C_{32}H_{24}N_6O_4$, calc m/e 556.1857; measured m/e 556.1909

Thermogravimetric analysis at 6°C/min. in nitrogen showed a sharp weight loss of 45% between 340°C. and 350°C., with no further loss up to 575°C. This coincides with the theoretical weight loss corresponding to the elimination of two moles of benzoic acid per mole of tetrabenzamidopyrazine.

Differential thermal analysis showed $T_{eo}$ (the temperature at the onset of the endotherm) = 340°C and $T_p$ = 343°C.

B. Preparation of 2,6-Diphenyl-1H,5H-diimidazo[4,5-b;4',5'-e] pyrazine:

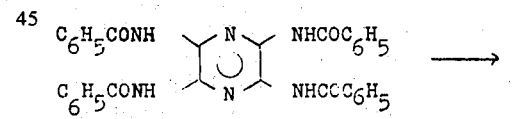

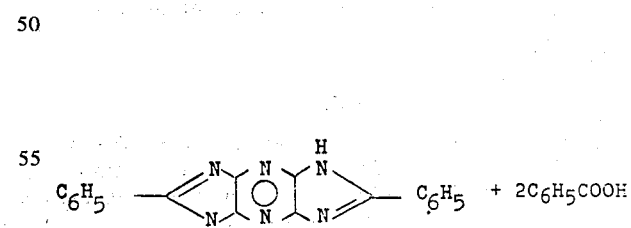

A glass tube open at one end was charged with 390 mg. of tetrabenzamidopyrazine and flushed with nitrogen. The closed end of the tube, containing the charge, was inserted in a cylindrical opening of a steel block capable of being heated electrically. The block was heated to 343°C. and held at that temperature for 15 minutes. As the temperature passed about 335°C., a volatile material was observed to condense as a crystalline solid in the cool portion of the tube. The tube was cooled under nitrogen and cut in half. The volatilized crystalline material was identified as benzoic acid by its infrared absorption spectrum. The non-volatilized material was 200 mg. (93%) of yellow, solid 2,6-diphenyl-1H,5H-diimidazo[4,5-b:4',5'-e]pyrazine.

Anal. Calcd. for $C_{18}H_{12}N_6$: C, 69.22; H, 3.87; N, 26.91. Found: C, 69.26; H, 3.79; N, 27.24; C, 69.00; H, 3.81, N, 27.18.

IR (KBr): 3.18μ (—NH): 6.19μ, 6.26μ, 6.41μ, 6.56μ, 6.79μ (aromatic —C=C— and —C=N—); 13.50μ, 14.53μ (monosubstituted aromatic).

The ultraviolet absorption spectrum was determined on a separate sample or the product prepared by essentially the foregoing method:

UV (λ max/DMSO): 405mμ ($k = 208$); 400mμ ($k = 206$); 386 mμ ($k = 194$); 317mμ ($k = 14.7$)

The product was slightly soluble in hot dimethylacetamide and hot hexamethyl(phosphorous triamide), and essentially insoluble in hot chloroform, hot water, hot benzene, and hot acetone. It dissolved in hot 10% aqueous sodium hydroxide, and yellow crystals appeared on cooling. Analysis indicated that the latter material was the disodium salt of the original product, in which two sodiums had replaced the two hydrogens bonded to nitrogen. Treatment of the disodium salt with water regenerated the original product. Solutions of the product in dimethylacetamide, hexamethyl(phosphorous triamide), and aqueous sodium hydroxide exhibited a deep-blue fluorescence.

C. A slurry was formed by heating briefly a mixture of 0.1 g of 2,6-diphenyl-1H,5H-diimidazo[4,5-b;4',5'-e]-pyrazine and 10 ml of dimethylformamide. The slurry was combined with 200 ml of hot water, and a multifiber swatch including fabrics of nylon, cotton, and viscose rayon was immersed in the liquid, which was then boiled for one hour. The swatch was removed, washed with hot water, washed with soap and water, rinsed with water, and dried in air. Under ultraviolet light the nylon fabric showed an intense blue fluorescence. D. Another slurry was formed by heating to boiling a mixture of 0.05 g or 2,6-diphenyl-1H,5H-diimidazo[4,5-b; 4',5'-e]pyrazine, 200 ml of water, and 1 ml of aqueous 10% sodium hydroxide. A multifiber swatch similar to that used in C above was immersed in the boiling mixture for 20 minutes and then washed, rinsed, and dried. The nylon, cotton, and viscose-rayon fabrics showed strong fluorescence under ultraviolet light.

EXAMPLE 2

A. In a manner similar to Example 1A, tetrakis(p-chlorobenzamidopyrazine was prepared from p-chlorobenzoyl chloride and tetraaminopyrazine in excess pyridine. The following data were obtained.

Anal. Calcd. for $C_{32}H_{20}Cl_4O_4N_6$: C, 55.4; H, 2.9; N, 12.1. Found: C, 54.0; H, 3.0; N, 12.0; C, 53.9; H, 3.0; N, 11.7.

Thermogravimetric analysis showed $T_p$ = ca. 420°C.

Another sample of this product, prepared essentially as described above, washed with hot acetone, and recrystallized from dimethyl sulfoxide, gave the following analysis:

Found: C, 55.1; H, 3.0; N, 12.1.

B. Preparation of 2,6-Bis(p-chlorophenyl)-1H,5H-diimidazo[4,5-b:4',5'-e]pyrazine

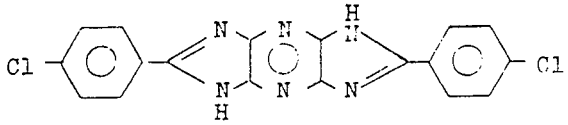

A sublimation apparatus was charged with 5.82 g of tetrakis(p-chlorobenzamido)pyrazine and thoroughly was with nitrogen. It was evacuated to about 300 mm pressure and immersed in a Wood's-metal bath that had been heated to 430°C. A volatile material (p-chlorobenzoic acid) sublimed rapidly. After 10 minutes the apparatus was removed from the bath and cooled. The non-volatile, greenish-yellow solid was washed with acetone and air-dried to give 3.30 g of product. The infrared absorption spectrum of the product indicated that some starting material was still present. The solid was returned to the sublimation apparatus, and the system was purged with nitrogen and heated for 10 minutes at about 300 mm pressure and a bath temperature of 430°–440°C. More sublimate was evolved during this time. The product was worked up as described above, and was 2.75g of greenish-yellow, solid 2,6-bis(p-chlorophenyl-1H,5H-diimidazo[4,5-b:4',5'-e]pyrazine. Its infrared absorption spectrum showed no absorption characteristic of the starting material. Part of the product was recrystallized from a large volume of dimethylformamide in the presence of activated charcoal, water being added to the filtrate to precipitate the product.

UV (λ max/DMSO): 411 mμ ($k$  109); 391 mμ ($k$ 93.6); 320 mμ ($k$  10.7).

Anal. Calcd. for $C_{18}H_{10}N_6Cl_2$: C, 56.71; H, 2.64; N, 22.05. Found: C, 56.98; H, 2.01; N, 21.60; C, 56.83; H, 2.88; N, 21.40.

EXAMPLE 3

A. In a manner similar to Example 1A, tetrakis(p-methoxybenzamido)pyrazine was prepared from p-methoxy-benzoyl chloride and tetraaminopyrazine in excess pyridine. The following data were obtained.

Anal. Calcd. for $C_{36}H_{32}O_8N_6$: C, 63.9; H, 4.8; N, 12.4. Found: C, 63.5; H, 4.6; N, 12.3; C, 63.5; H, 4.7; N, 12.2.

Thermogravimetric analysis showed $T_p$ = ca. 370°C.

B. Preparation of 2,6-bis(p-methoxyphenyl)-1H,5H-diimidazo[4,5-b:4',5'-e]pyrazine

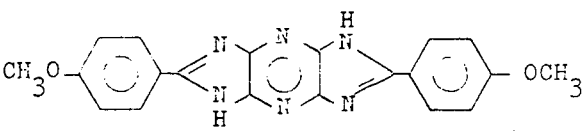

A sublimation apparatus in which the sublimand could be charged in a thin layer was charged with 5.95 g of tetrakis(p-methoxybenzamido)pyrazine and thoroughly purged with nitrogen. The apparatus was placed in a Wood's-metal bath that had been heated to 370°C. and was left there for 5 minutes, during which time the bath temperature rose to 400°C. and a sublimate appeared. The apparatus was cooled, and the non-volatilized material was found to weight 5.02 g. Since this was more than the theoretical yield of the diimidazopyrazine, the material was returned to the sublimation apparatus. The apparatus was purged with nitrogen and, under partial evacuation to a pressure of about 300 mm, inserted in the bath at 405°C. After 3 to 5 minutes the system was cooled, and the non-volatilized solid was washed with acetone and dried, to give 2.86 g of crude 2,6-bis(p-methoxyphenyl)-1H,5H-diimidazo[4,5-b:4',5'-e]pyrazine as a glossy, metallic-looking solid. It appeared that a small amount of the product had sublimed along with the by-product, p-methoxybenzoic acid. The product was(partly) extracted with acetone in a Soxhlet extractor. Each fresh extract showed a greenish fluorescence, and after 5 days 0.70 g of orange diimidazopyrazine had been extracted. The infrared absorption spectrum of the extract was essentially the same as that of the "crude" product.

Anal. Calcd. for $C_{20}H_{16}O_2N_6$: C, 64.51; H, 4.33. Found: C, 64.41; H, 4.55; C, 64.21; H, 4.52.

EXAMPLE 4

A. In a manner similar to Example 1A, tetraacetamidopyrazine was prepared from acetyl chloride and tetraaminopyrazine in excess pyridine. The following data were obtained.

Anal. Calcd. for $C_{12}H_{16}O_4N_6$: C, 46.8; H, 5.2; N, 27.3. Found: C, 45.4; H, 4.7; N, 26.6; C, 45.6; H, 5.2; N, 26.6; C, 45.8; H, 5.1; N, 26.8.

Thermogravimetric analysis showed $T_p$ = ca. 285°C.

B. Preparation of 2,6-dimethyl-1H,5H-diimidazo[4,5-b:4',5'-e]pyrazine

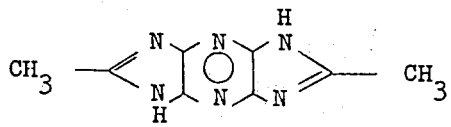

An apparatus like that of Example 1 was charged with 2.0 g of tetraacetamidopyrazine, purged with nitrogen, and heated at 280°–285°C. for 5 minutes, during which time acetic acid volatilized and condensed. The tube was cooled, the condensate was separated, the non-volatile material was stirred with a glass rod, and heating was continued for two minutes more. On cooling there was obtained 0.75 g of crude 2,6-dimethyl-1H,5H-diimidazo[4,5-b:4',5'-e]pyrazine as a brown solid. The product was dissolved in 30 ml of aqueous 10% sodium hydroxide, and the hot solution was treated with activated charcoal and filtered. On cooling, the yellow, intensely blue-fluorescent solution deposited yellow needles of the sodium salt of the diimidazopyrazine, which were separated by filtration and dried. The crystals were slurried with 10 ml of water, in which they partly dissolved to give a yellow solution with an intense blue fluorescence to ultraviolet light. The slurry was carefully acidified to a pH of 1 with 2 N HCl, whereupon the diimidazopyrazine precipitated as a cream-colored solid. After standing overnight the mixture was filtered, and the product was washed with water, washed with a little methanol, and dried.

Anal. Calcd. for $C_8H_8N_6$: C, 51.95; H, 4.28; N, 44.66. Found: C, 50.49; H, 4.29; N, 44.71; C, 50.33; H, 4.20; N, 44.79.

UV ($\lambda$ max/DMSO): 343 m$\mu$ ($k$ = 136); 337 m$\mu$ ($k$ = 131)

EXAMPLE 5

This example illustrates the use of a diluent. A slurry of 2.50 g of tetrakis(p-methoxybenzamido)pyrazine, prepared in Example 3A, in 10 g. of phenyl sulfone was heated rapidly to reflux (368°C.) under nitrogen. When the temperature passed about 270°C., the mixture became homogeneous for a short time, after which a solid precipitated. After 5 minutes at reflux, the mixture was allowed to cool to near room temperature. The mixture was removed from the reaction vessel with the aid of 100 ml. of hot benzene, and the solid was separated by filtration. The solid was washed with 50 ml. of hot benzene and air-dried to give 1.14 g. (76%) of 2,6-bis(p-methoxyphenyl)-1H,5H-diimidazo[4,5-b:4',5'-e]pyrazine as greenish-yellow crystals.

Anal. Calcd. for $C_{20}H_{16}N_6O_2$: C, 64.51; H, 4.33; N, 22.57. Found: C, 64.50; H, 4.28; N, 22.30; C, 64.92; H, 4.50; N, 22.27.

The ultraviolet absorption spectrum was measured in hexamethyl-(phosphorous triamide):

UV ($\lambda$ max/HMPA):414 m$\mu$ ($k$ = 109); 394 m$\mu$ ($k$ = 97.2)

EXAMPLE 6

A. In a manner similar to Example 1A, tetrakis(1-naphthamido)pyrazine was prepared from 1-naphthoyl chloride and tetraaminopyrazine. It showed the expected infrared absorption spectrum and had a $T_p$ of ca. 340°C.

B. Preparation of 2,6-bis(1-naphthyl)-1H,5H-diimidazo[4,5-b:4',5'-e]pyrazine.

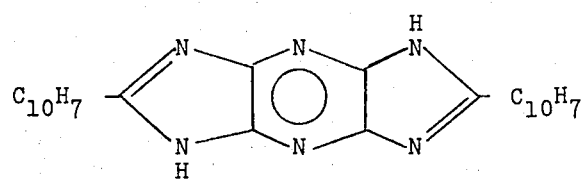

A mixture of 5.0 g. of tetrakis(1-naphthamido)pyrazine and 20 g. of phenyl sulfone was heated with stirring under nitrogen to 360°C over a period of 1.5 hours. The mixture was allowed to cool and was removed from the reaction vessel with the aid of 400 ml. of hot benzene, and the solid was separated by filtration. The solid was washed with 100 ml. more of hot benzene and air-dried to give 2.23 g. of solid 2,6-bis(1-naphthyl)-1H,5H-diimidazo[4,5-b:4',5'-e]pyrazine. The infrared absorption spectrum of the product was much like that of the product of Example 1B. The product was recrystallized by dissolving 2.0 g. of it in 1200 ml. of hot aqueous 8.5% potassium hydroxide. The hot solution had a strong green fluorescence in ordinary light. Activated charcoal was added, and the hot mixture was filtered and cooled, whereupon the potassium salt of the diimidazopyrazine crystallized in maroon needles. The salt was separated by filtration after cooling the mixture in ice. It was acidified with excess 2NHCl, the resulting slurry was filtered, and the solid on the filter was washed with water, washed with acetone, and dried to give orange-yellow 2,6-bis(1-naphthyl)- 1H,5H-diimidazo[4,5-b:4',5'-e] pyrazine.

Anal. Calcd. for $C_{26}H_{16}N_6$: C, 75.71; H, 3.91; N, 20.38. Found: C, 74.85; H, 3.65; N, 20.30; C, 74.90; H, 3.67; N, 21.13; N, 20.33.

UV (λ max/HMPA): 400 mµ (k = 125)

Other diimidazopyrazines of the invention can be made from the appropriate acid chlorides and tetraaminopyrazine by the methods illustrated in the foregoing examples. For example, the reaction of 2-ethylhexanoyl chloride with tetraaminopyrazine in excess pyridine will give tetrakis(2-ethylhexanamido)pyrazine. Pyrolysis of the latter at or near its decomposition temperature will give 2,6-bis(1-ethylpentyl)-1H,5H-diimidazo[4,5-b:4′,5′-e]pyrazine.

Similarly, tetrakis(p-fluorobenzamido)pyrazine can be prepared by reacting p-fluorobenzoyl chloride with tetraaminopyrazine in excess pyridine. Pyrolysis at or near its $T_p$ will give 2,6-bis(p-fluorophenyl)-1H,5H-diimidazo[4,5-b:4′,5′-e]pyrazine.

In the same way, reaction of 4-biphenylcarbonyl chloride with tetraaminopyrazine in excess pyridine will give tetrakis(4-biphenylcarboxamido)pyrazine. Heating this compound at or near its $T_p$ will give 2,6-bis(4-biphenylyl)-1H,5H-diimidazo[4,5-b:4′,5′-e]pyrazine.

The by-product carboxylic acids obtained in the formation of the foregoing three diimidazopyrazines are, respectively, 2-ethylhexanoic acid, p-fluorobenzoic acid, and 4-biphenylcarboxylic acid.

In the same way that diimidazopyrazines of the invention containing substituted phenyl groups in the 2- and 6-positions can be made from the appropriately substituted benzoyl chlorides, products containing substituted naphthyl groups and substituted biphenylyl groups in the 2- and 6-positions can be made by starting with the appropriately substituted naphthoyl chlorides and biphenylcarbonyl chlorides.

Although the invention has been described and exemplified by way of specific embodiments, it is not intended that it be limited thereto. As will be apparent to those skilled in the art, numerous modifications and variations of these embodiments can be made without departing from the spirit of the invention or the scope of the following claims.

The embodiments of the invention in which an exclusive property or privilege is claimed are defined as follows:

1. A diimidazopyrazine of the formula

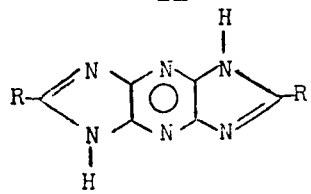

wherein the R's are the same and are selected from the group consisting of lower alkyl of up to 8 carbons, aryl hydrocarbon of 6 to 12 carbons, and aryl hydrocarbon of 6 to 12 carbons substituted with up to two substituents selected from the group consisting of lower alkyl of up to 8 carbons, lower alkoxy of up to 8 carbons, phenoxy, bromo and nitro or up to five substituents selected from the group consisting of fluoro and chloro.

2. The diimidazopyrazine of claim 1 wherein R is phenyl.

3. The diimidazopyrazine of claim 1 wherein R is p-chlorophenyl.

4. The diimidazopyrazine of claim 1 wherein R is p-methoxyphenyl.

5. The diimidazopyrazine of claim 1 wherein R is methyl.

6. A tetra-substituted-amidopyrazine of the formula

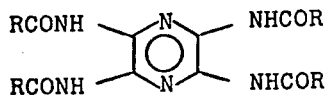

wherein the R's are the same and are selected from the group consisting of lower alkyl of up to 8 carbons, aryl hydrocarbon of 6 to 12 carbons, and aryl hydrocarbon of 6 to 12 carbons substituted with up to two substituents selected from the group consisting of lower alkyl of up to 8 carbons, lower alkoxy of up to 8 carbons, phenoxy, bromo and nitro, or up to five substituents selected from the group consisting of fluoro and chloro.

7. The amidopyrazine of claim 6 wherein R is phenyl.

8. The amidopyrazine of claim 6 wherein R is p-chlorophenyl.

9. The amidopyrazine of claim 6 wherein R is p-methoxyphenyl.

10. The amidopyrazine of claim 6 wherein R is methyl.

* * * * *